(12) United States Patent
Volodin et al.

(10) Patent No.: US 8,553,221 B2
(45) Date of Patent: *Oct. 8, 2013

(54) COMPACT, LOW COST RAMAN MONITOR FOR SINGLE SUBSTANCES

(75) Inventors: Boris Leonidovich Volodin, West Windsor, NJ (US); Vladimir Sinisa Ban, Princeton, NJ (US)

(73) Assignee: PD-LD, Inc., Pennington, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/547,469

(22) Filed: Jul. 12, 2012

(65) Prior Publication Data

US 2013/0182247 A1   Jul. 18, 2013

Related U.S. Application Data

(63) Continuation-in-part of application No. 13/361,072, filed on Jan. 30, 2012, now Pat. No. 8,339,598, which is a continuation of application No. 13/165,333, filed on Jun. 21, 2011, now Pat. No. 8,125,635, which is a continuation of application No. 11/923,571, filed on Oct. 24, 2007, now Pat. No. 7,982,869.

(60) Provisional application No. 60/854,339, filed on Oct. 24, 2006.

(51) Int. Cl.
*G01J 3/44*   (2006.01)

(52) U.S. Cl.
USPC ........... 356/301; 356/302; 356/603; 700/182; 700/117

(58) Field of Classification Search
USPC ................ 356/603, 302, 631; 700/117, 119, 700/103, 97
See application file for complete search history.

(56) References Cited

U.S. PATENT DOCUMENTS

| 6,671,083 | B2 | 12/2003 | Tanaka et al. |
| 6,958,856 | B2 | 10/2005 | Inoue et al. |
| 7,031,573 | B2 | 4/2006 | Volodin et al. |
| 7,125,632 | B2 | 10/2006 | Volodin et al. |
| 7,411,670 | B2 | 8/2008 | Zribi et al. |
| 7,443,895 | B2 | 10/2008 | Schulte et al. |
| 7,583,710 | B2 | 9/2009 | Dantus et al. |
| 8,339,598 | B2 * | 12/2012 | Ban et al. ...................... 356/301 |
| 2005/0018743 | A1 | 1/2005 | Volodin et al. |

* cited by examiner

*Primary Examiner* — Gregory J Toatley
*Assistant Examiner* — Iyabo S Alli
(74) *Attorney, Agent, or Firm* — Condo Roccia LLP

(57) ABSTRACT

Apparatus for performing Raman spectroscopy may include a first laser source having a first emission wavelength and a second laser source having a second emission wavelength. A separation between the first and second emission wavelengths may correspond to a width of a Raman band of a substance of interest. An optical switch may provide switching between the first and second laser sources. An ensemble of individually addressable laser emitters may be provided. A Bragg grating element may receive laser light from the ensemble. An optical system may direct light from the Bragg grating element into an optical fiber. A combined beam through the optical fiber may contain light from each of the emitters.

20 Claims, 9 Drawing Sheets

COMPACT, LOW COST RAMAN MONITOR FOR SINGLE SUBSTANCES

CROSS-REFERENCE TO RELATED APPLICATIONS

This application is continuation-in-part of U.S. patent application Ser. No. 13/361,072, filed Jan. 30, 2012, which is a continuation of U.S. patent application Ser. No. 13/165,333, filed Jun. 21, 2011, now U.S. Pat. No. 8,125,635, which is a continuation of U.S. patent application Ser. No. 11/923,571, filed Oct. 24, 2007, now U.S. Pat. No. 7,982,863, which claims benefit under 35 U.S.C. §119(e) of provisional U.S. Patent Application No. 60/854,339, filed Oct. 24, 2006, the disclosure of which is incorporated herein by reference in its entirety.

BACKGROUND

Raman analysis is a well-known analytical technique used for structural analysis of molecular species. Raman analysis exploits the inelastic scattering of light by a substance that carries information about the vibrational spectrum of the constituent molecular compounds. The distinguishing feature of Raman analysis compared with, for example, infrared (IR) or near infrared (NIR) absorption vibrational spectroscopy is the fact that the optical excitation of the sample is done at a much shorter wavelength of light and the corresponding Raman signal is emitted in the spectral band of a much shorter wavelength than the IR absorption lines of the same sample. This feature allows efficient analysis of aqueous solutions and also makes it possible to construct very compact instruments.

Typical Raman systems employed so far use a monochromatic source of incident radiation such as a laser combined with a spectrometer and a detection system such as a CCD camera (dispersive Raman). Another type of a conventionally used Raman system is Fourier transform Raman that uses a scanning interferometer and a single detector for spectral analysis. Lasers that are used for Raman analysis typically emit in the visible, near infrared, or near ultraviolet spectrum. Many variations of radiation detectors have been used in the art, ranging from photomultiplier tubes to CCD cameras.

Traditionally, the cost of Raman spectrometers has been driven by the cost of the laser excitation source, the spectrometer that may use notch filters designed to suppress Rayleigh scattering, cooled CCD camera and the signal analysis module that usually requires a fully functional computer, operating system and specialized software. Some Raman systems also employ a fiber-optic probe for delivering laser light to the sample and collecting the Raman signal.

SUMMARY OF THE INVENTION

The invention provides apparatus and methods for Raman analysis using three-dimensional Bragg grating elements in combination with commercially available lasers and detectors to perform quantitative analysis of various types of samples with respect to select substances of interest. Three-dimensional Bragg gratings have been previously described, for example, in U.S. Pat. No. 7,031,573, the disclosure of which is incorporated herein by reference.

By utilizing three-dimensional Bragg grating elements the size and cost of a Raman system can be drastically reduced. Three-dimensional Bragg grating elements can be used to produce a stable laser source suitable for Raman analysis out of mass-produced laser diodes that are used, for example, in CD and DVD drives. They can also be used to filter Rayleigh scattering by manufacturing ultra-narrow notch filters using that technology, and to analyze the Raman spectra scattered from the sample material. Both reflective and transmissive Bragg gratings can be used in construction of various embodiments of the disclosed invention.

By combining three-dimensional Bragg grating elements with mass-produced lasers and detectors, high-quality Raman-scattering sensors can be produced at a reasonable cost, making more accessible their use in everyday applications such as airport security, law enforcement, medical diagnostics, manufacturing quality testing, explosive detection etc. The three-dimensional Bragg grating elements enable the use of much smaller components then used in conventional dispersive Raman systems, which can result in Raman instruments as small as a few cubic centimeters in size. Smaller instruments can be used in Raman sensor devices such as wearable personal detection devices.

Such Raman monitors can be tuned to detect specific molecular species of interest and perform quantitative analysis of their content. By monitoring only certain bands of the Raman spectral range where peaks for select substance(s) of interest appear, small Raman instruments enabled by the technology of the three-dimensional Bragg gratings can be built to detect the presence of the target substance(s). For example, it may be desirable to build sensors capable of alerting the user of the presence of a harmful contaminant or bacteria such as Anthrax. The potential usefulness of such targeted sensor devices in applications related to monitoring for toxins, spores, pollutants and allergens is evident.

By exploiting known Raman spectra of different substances, devices can be built using three-dimensional Bragg gratings that can analyze the content of select substance(s) in a mixed sample that produces convoluted Raman spectra. For example, in a very simple case when a sample contains two substances, one with a characteristic spectrum of five peaks in five spectral bands and one with six peaks in other spectral bands, an instrument can be developed using three-dimensional Bragg gratings as filters. If the filters are placed such that all five peaks appear in the five detectors, the device unambiguously identifies the first substance. In more complex cases a statistical analysis may be carried out using appropriate methods (including but not limited to partial least squares, multiple linear regression, neural nets, principal component regression etc.) to select best parameters for quantitative analysis.

In a simple example, the positions of the valleys in the Raman spectrum of the molecular species of interest also carry important information. For that reason one band or multiples bands may be added to the spectrum analysis module that correspond to the position of the spectral valleys. These bands are important to differentiate the Raman signal from its background that may be caused, for example, by fluorescence. These spectral bands allow providing quantitative information about the amount of the detected substance in the sample.

In some embodiments, inelastically-scattered light is separated from elastically-scattered light by a signal separation block to yield the Raman signal. The Raman signal is separated (or demultiplexed) into specific bands by a spectrum analysis module. The spectrum analysis module, which in some embodiments is a demultiplexer, may be constructed using three-dimensional Bragg grating elements to direct each of the selected spectral bands of the Raman signal to a detector that monitors the intensity of that selected spectral band. In different embodiments, demultiplexers using three-dimensional Bragg gratings or other suitable technologies can be used to separate the various spectral bands of the Raman signal and direct each band to the appropriate detector for monitoring. A multi-band filter or several such filters can also be constructed using the technology of three-dimensional Bragg gratings to filter out multiple select bands from the broad band signal and direct the filtered light to a detector or several detectors. Optimal construction of such filters will depend on the results of statistical analysis of a particular chemometrics problem with respect to the best combination of parameters for quantitative prediction.

A variety of software functions that can also be implemented in programmable logic circuits may be used to process the signal from the Raman sensor instrument and provide the detection of species in the sample.

DETAILED DESCRIPTION OF ILLUSTRATIVE EMBODIMENTS

Figure 1A:
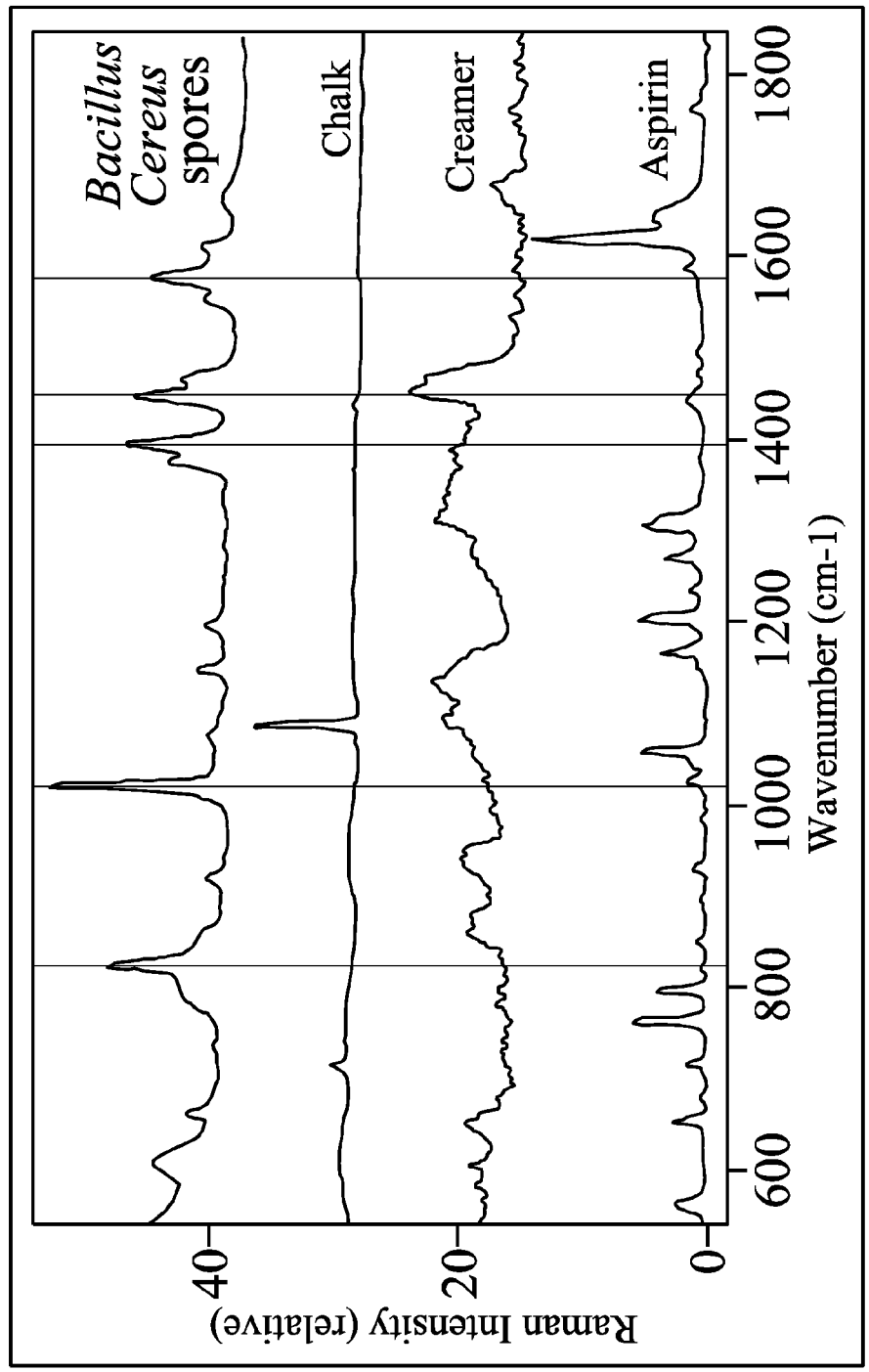
FIGS. 1A and 1B provide examples of Raman spectra for various substances.
Figure 1B:
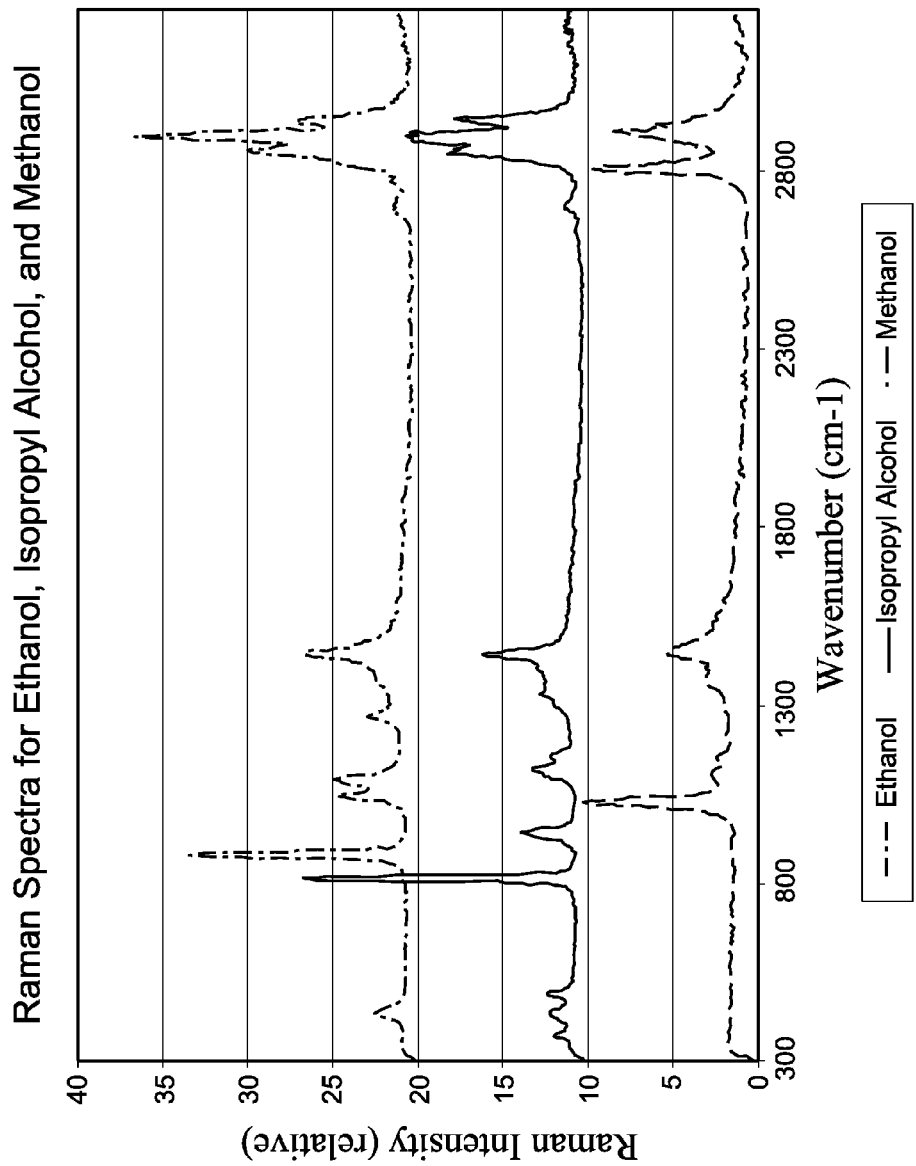

Detection methods based on Raman analysis have superior specificity since any molecule unique in structure will have a corresponding unique combination of vibrational modes. However, among the multitude of these modes there is usually a significantly smaller number that best distinguish the unique character of the molecule. These modes may correspond to certain collective motions of the atoms unique to their spatial positions relative to each other. These modes may, therefore, be called "Raman signature lines" of a particular molecule. The number of these signature lines may be different for each molecule but it is generally a substantially smaller number than that contained in its entire Raman spectrum. For example, FIG. 1B shows Raman spectra of light alcohols that clearly show that a few select spectral bands can be used for differentiation between these substances. Successful detection of practically any molecule can be carried out by performing correlation of only a small subset of the Raman-active lines in the vibrational spectrum of a sample under study with that of a pure substance of interest.

This approach greatly simplifies the design of a Raman sensor and allows efficient use of inexpensive components, such as mass-produced laser diodes, PIN photo-diodes, and three-dimensional Bragg gratings. It also eliminates the use of a computer with operating system and sophisticated software that typically add cost, consume a lot of power and typically require long times for processing of each sample.

The components of a Raman sensor can be realized by combining mass-produced semiconductor lasers and detectors with three-dimensional Bragg grating elements. For example, a Raman laser source and Raman spectrum detection system can be produced using such combinations. Because these components are small in size, Raman instruments can be produced that are exceptionally small, even as small as a few cubic centimeters. Due to wafer-scale efficient reproduction methods for three-dimensional Bragg grating elements, the cost of these instruments may be kept very low that enables their application as Raman monitors in a wide range of areas including buildings, public spaces, vehicles, and even personal devices.

By using this technology, Raman sensors may be designed that monitor specific spectral lines that may, for example, corresponding to Raman signature of any substance(s) of interest and a particular laser excitation wavelength. Another example of Raman spectra of several compounds is shown in FIG. 1A. Different spectral patterns are shown for the picolinic acid produced by bacterial spores such as anthrax (*bacillus cereus*), chalk, aspirin, and creamer. The distinct pattern of Raman signature lines for the substance associated with bacteria spores can be readily distinguished. These five prominent Raman bands can thus be used to differentiate bacterial spores from other white powders in an embodiment of the invention that is adapted to serve as a Raman monitor for this substance. By using five Bragg grating elements, each of which allows passage of one and only one of the spectral bands of the Raman signature into each of five detectors, a signal from the five detectors can unambiguously identify the substance by its characteristic Raman lines. Thus, a device according to the invention may be adapted to monitor for a specific substance or several substances.

Additionally, such a device may be adapted to detect spectral bands that correspond to valleys (or areas of absence of Raman peaks) in the Raman spectrum of substance(s) of interest. This allows monitoring the intensity of a background signal, fluorescence, or any other noise-contributing signals. Determining background signal level may be useful in quantitative monitoring of a substance of interest through calculations that subtract the noise contribution from the signal, for example, to determine the concentration of the analyte in a sample.

FIG. 2 is a functional block diagram of an example embodiment of a Raman analysis system 100 comprising a plurality of three-dimensional Bragg grating elements. Examples of such three-dimensional Bragg gratings, and methods for making the same, are described, for example, in U.S. Pat. No. 7,031,573.

Such a system 100 may include a laser source 102 that emits laser light 104. The laser source 102 may be a commonly found semiconductor 120-mW, 785-nm laser source. It should be understood that laser source 102 may emit laser light 104 of any desired wavelength, such as, for example, 630 nm, 830 nm, 980 nm, or 1064 nm. The laser source 102 may be a frequency-doubled laser source, such as disclosed in U.S. patent application Ser. No. 10/884,524, the disclosure of which is incorporated herein by reference. The laser source 102 may be an ultra-violet laser source. The laser power may be in a range from mW to Watts, as desired for a particular application. The laser light 104 may be delivered continuously or in pulsed mode. For more complex Raman analysis, several different wavelength sources may be combined. For example, by using two close-excitation wavelengths, it is possible to subtract the fluorescence background because it is independent of the excitation wavelength. This approach relies on the fact that Raman spectrum lines always shift together with the wavelength of the excitation laser, whereas the fluorescence and other background sources are independent of the wavelength of the excitation laser.

Figure 5:
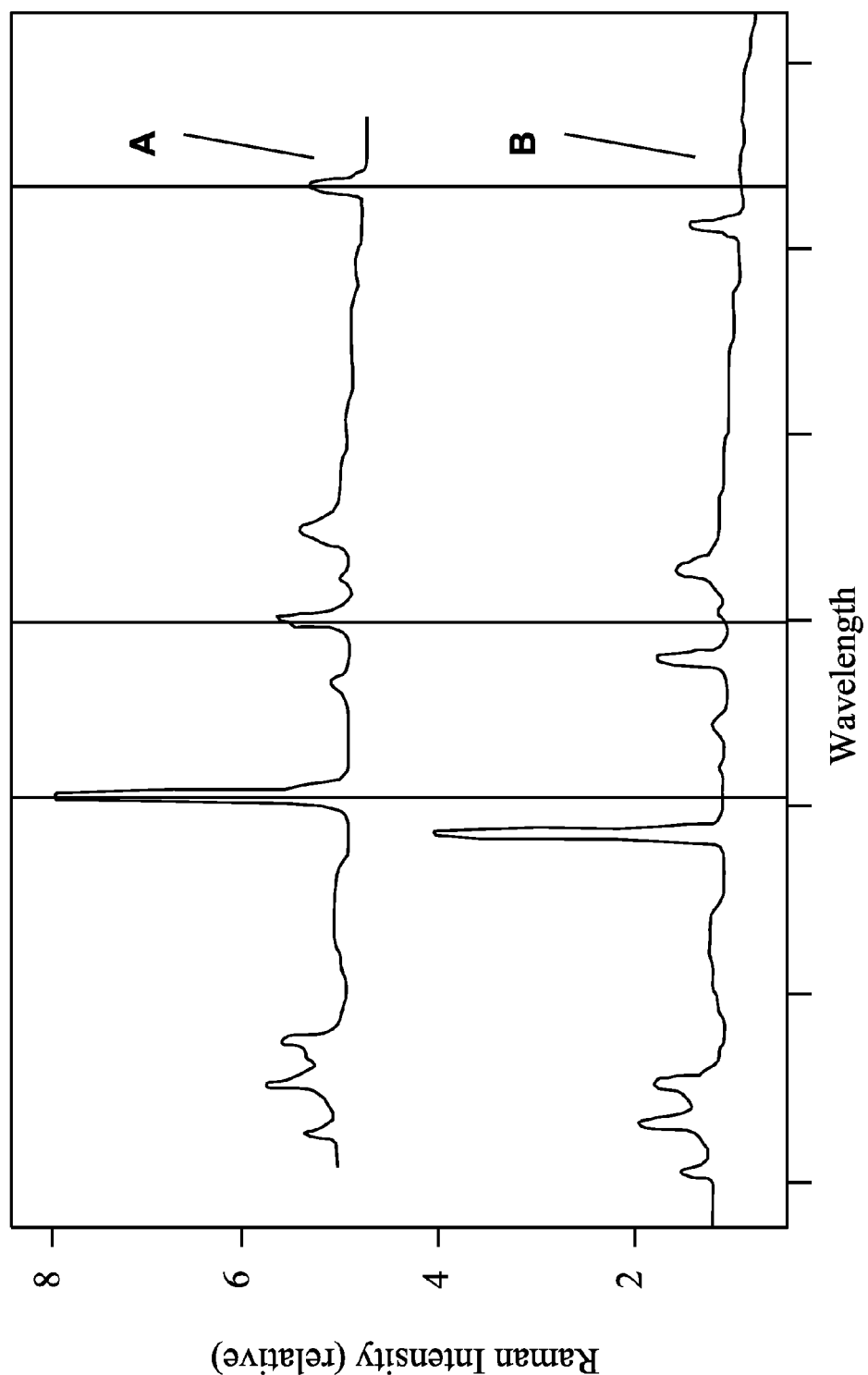
FIG. 5 provides Raman spectra produced by two laser sources with different emission wavelengths.

Therefore, in this approach two laser sources with closely spaced emission wavelengths may be used. The separation between two wavelengths may be selected to approximately correspond to the width of the lines in the Raman spectrum of the substance of interest. Raman scattering may then be collected through the same optical system when the two laser sources excite the sample sequentially. In this case, as shown in FIG. 5, the detectors aligned with different wavelength channels of the spectrum analysis module (demultiplexer) may detect the peaks of the Raman bands of the substance of interest when laser 1 is firing (designated "A" in FIG. 5) and detect the valleys of the same spectrum when laser 2 is firing (designated "B" in FIG. 5). Since the background light is independent of the excitation wavelength, its contribution to the signal remains the same. As a result, when a subtraction of the two sets of measurements is performed the result is background-free set of values representing true amplitudes of the Raman peaks of the selected substance.

Figure 6:
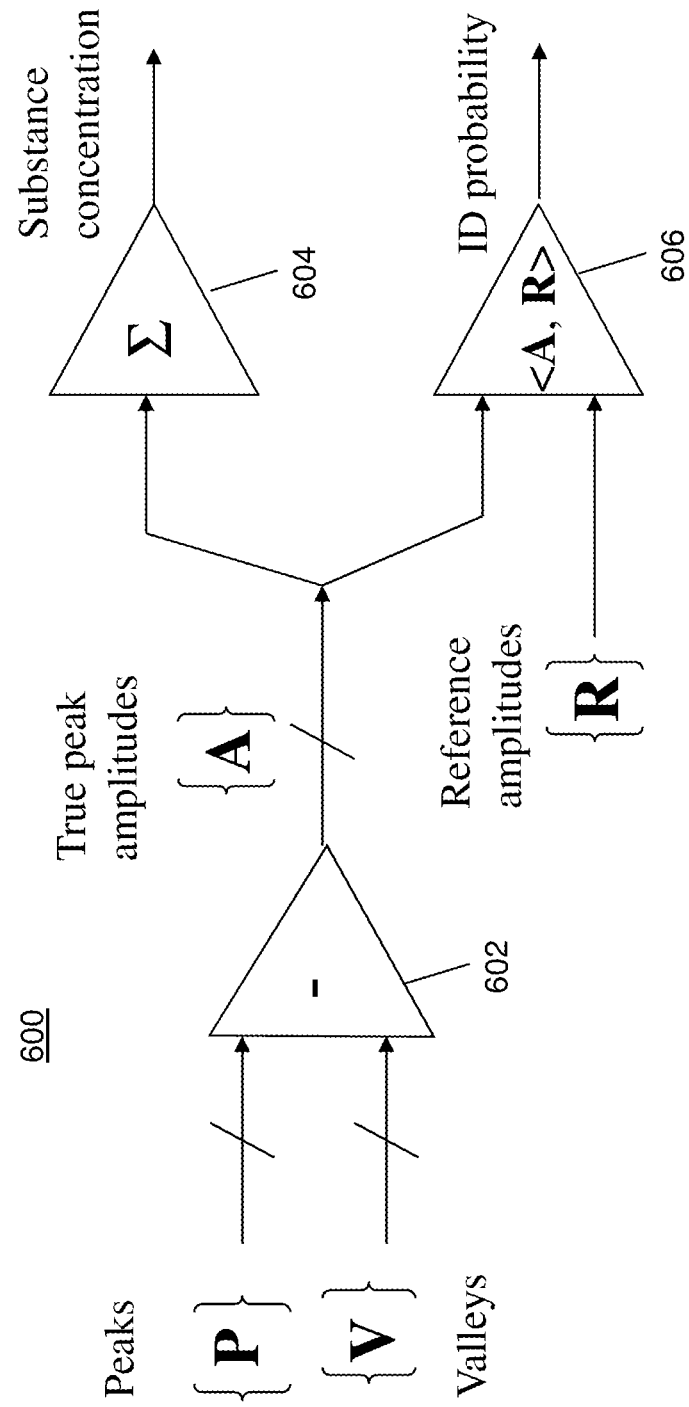
FIG. 6 depicts an example circuit for analysis of a collected signal.

Based on this approach a simple circuit may be constructed for analysis of the collected signal. Such a circuit is depicted in FIG. 6. In this circuit 600, the collected data arrays are first subtracted, at 602, and then directed to two channels—the summation channel 604 and the correlation channel 606. In the correlation channel 606, a simple computation of a correlation coefficient between the collected background-free set of peaks and the stored array of true peak amplitudes for the pure compound of interest is performed. The output of the correlation channel 606 is a single value representing the probability of identification of the selected compound in the sample under study. On the other hand, in the summation channel 604 the sum of all true peak amplitudes is computed that is proportionate to the amount of the analyte present in the sample.

Figure 2:
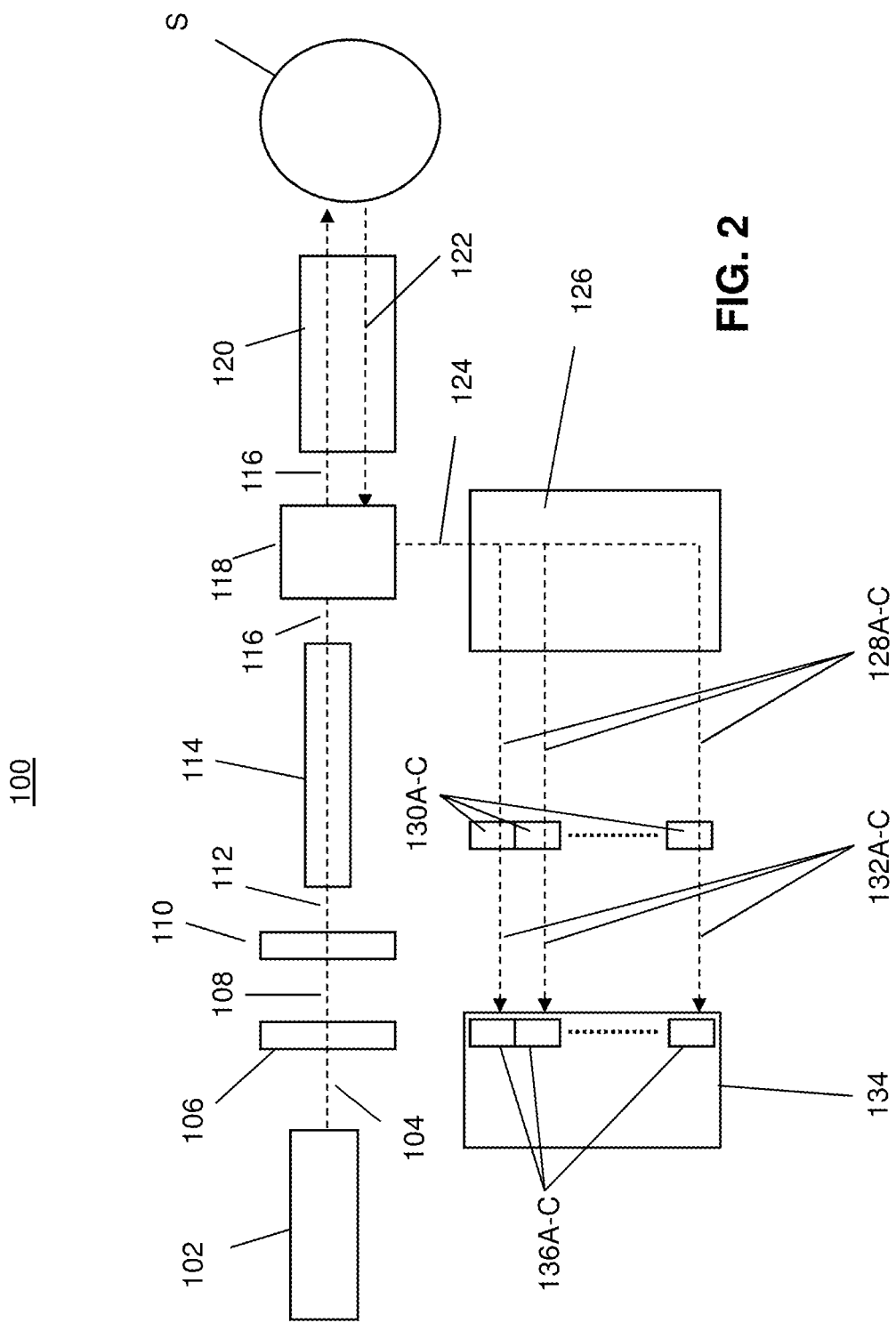
FIG. 2 is a functional block diagram of a Raman spectrometer that includes a plurality of three-dimensional Bragg grating elements.

With reference once again to FIG. 2, a first three-dimensional Bragg grating element 106 may be positioned to receive the laser light 104. The element 106 may be adapted to condition the laser light 104, such as, for example, by narrowing the bandwidth of the emitted laser light 104. The element 106 may also be adapted to control the central wavelength of the emitted light 104. By conditioning the emitted laser light 104, the element 106 may adapt a commonly found semiconductor laser 102 for use as a Raman source.

The conditioned laser light 108 may be received by a band pass filter 110. The filter 110 may be adapted for "laser line" filtering. That is, the band pass filter 110 may allow the passage of a narrowband beam 112, which may have a bandwidth of, for example, approximately 1 nm. The band pass filter 110 may suppress stray light outside the desired band. The band pass filter 110 may include a thin film interference filter, for example, or a three-dimensional Bragg grating element adapted to produce a desired beam. Either a transmissive or reflective Bragg grating element may be used. The band pass filter 110 may have any desired characteristics, such as width, transparency, side mode suppression, filter shape, physical size and shape, etc. The characteristics of the filter may be adapted to determine stray light levels, sensitivity, resolution, and the like.

The narrowband beam 112 may be received by a beam delivery system 114. The beam delivery system 114 may include free-space delivery of a collimated beam to a sample S that is monitored at close range. The beam delivery system 114 may include telescopic or microscopic optics. The beam delivery system 114 may include a fiber-optic beam delivery system, or any other optics system that is adapted to propagate a Raman signal.

The beam delivery system 114 may deliver Raman source light 116 to a Raman spectra sampling head 120. The Raman sampling head 120 may be designed to allow sampling at close range or from a distance. It is further possible to include Surface Enhanced Raman Spectroscopy (SERS) substrates that can enhance the signal. The signal could also be enhanced by using methods of sample collection such as gaseous sampling, pumping, and swabbing of the sample. The sampling head 120 may be adapted for use with solid, liquid, or gaseous samples. The sampling head 120 may come into direct contact with a sample S, or be coupled to the sample S via a transparent window or other optical device. The sampling head 120 may include telescopic or microscopic elements that are suitable for remote sensing of the substance. Either the sample head 120 or the sample S may be movable for such applications as raster scanning.

A signal separator 118 may be adapted to separate the scattered laser source light 116 from Raman signal light 122 that is scattered by the sample S. As shown, the signal separator 118 may be positioned between the beam delivery system 114 and the Raman sample head 120. The signal separator 118 may receive the Raman source light 116 from the beam delivery system 114, and the Raman sampling head 120 may receive the Raman source light 116 from the signal separator 118.

The signal separator 118 may include a three-dimensional Bragg grating element, which may be adapted to perform as a narrowband notch filter. To reduce Rayleigh scattering that can enter the detection system, the notch filter may allow passage only of light having a bandwidth that matches the line width of the excitation laser 102. Thus, stray light may be decreased, and the signal-to-noise ratio improved. Other well-known technologies may also be used, for example thing film dielectric filters and dichromated gelatin holographic filters.

The signal separator 118 may be positioned to receive a Raman signal 122 that is scattered from the sample S. The signal separator 118 may be adapted to separate inelastically-scattered light 124 in the Raman signal 122 from elastically-scattered light at the same wavelength as the laser source 102.

The signal separator 118 may be adapted to direct the inelastically-scattered light 124 into a demultiplexer 126. The demultiplexer 126 may include one or more Bragg gratings that cooperate to separate one or more Raman bands 128A-C from the received portion 124 of the Raman signal 122. The demultiplexer 126 may include a plurality of discrete Bragg grating elements. In such an embodiment, each Bragg grating element may have recorded thereon a respective Bragg grating that redirects any portion of the received light that falls within a certain desired Raman band. Each Bragg grating element may be transparent to the remainder of the light it receives. The demultiplexer 126 may include a Bragg grating chip, which may be a single bulk of material having a plurality of Bragg gratings recorded therein. Each Bragg grating may be adapted to redirect any portion of the received light that falls within a certain desired Raman band, and to transmit the remainder of the light it receives to another Bragg grating within the chip. Three-dimensional Bragg grating chips are disclosed in U.S. Pat. No. 7,125,632, the disclosure of which is incorporated herein by reference.

Each Raman band 128A-C may be directed through a respective Raman band pass filter 130A-C. Each such filter 130A-C may be a band pass filter with strong side mode suppression to further reduce stray light in the beam 128A-C.

The width of the passband and the form of the filter may be designed for a particular application. One or more Bragg grating elements may be adapted for this purpose. The filters 130A-C may have different characteristics, such as width, transparency, side mode suppression, filter shape, physical size and shape, etc. The characteristics of the filter used will aid in determining the characteristics of the instrument. A number of Bragg grating filters may be placed in series in order to further suppress stray light or influence the selectivity and resolution of the Raman monitor.

The filtered Raman bands 132A-C may be directed into a detector system 134, which may include one or more detectors 136A-C. Each band 132A-C may be directed into a respective detector 136A-C. Each such detector 136A-C may be adapted to determine a signal intensity level associated with the received Raman band 132A-C. The detectors 136A-C may be discrete Si or InGaAs pin detectors, APD detectors, or the like. Detector arrays may be constructed in two or three dimensions to allow for spectral imaging of the sample.

Figure 3:
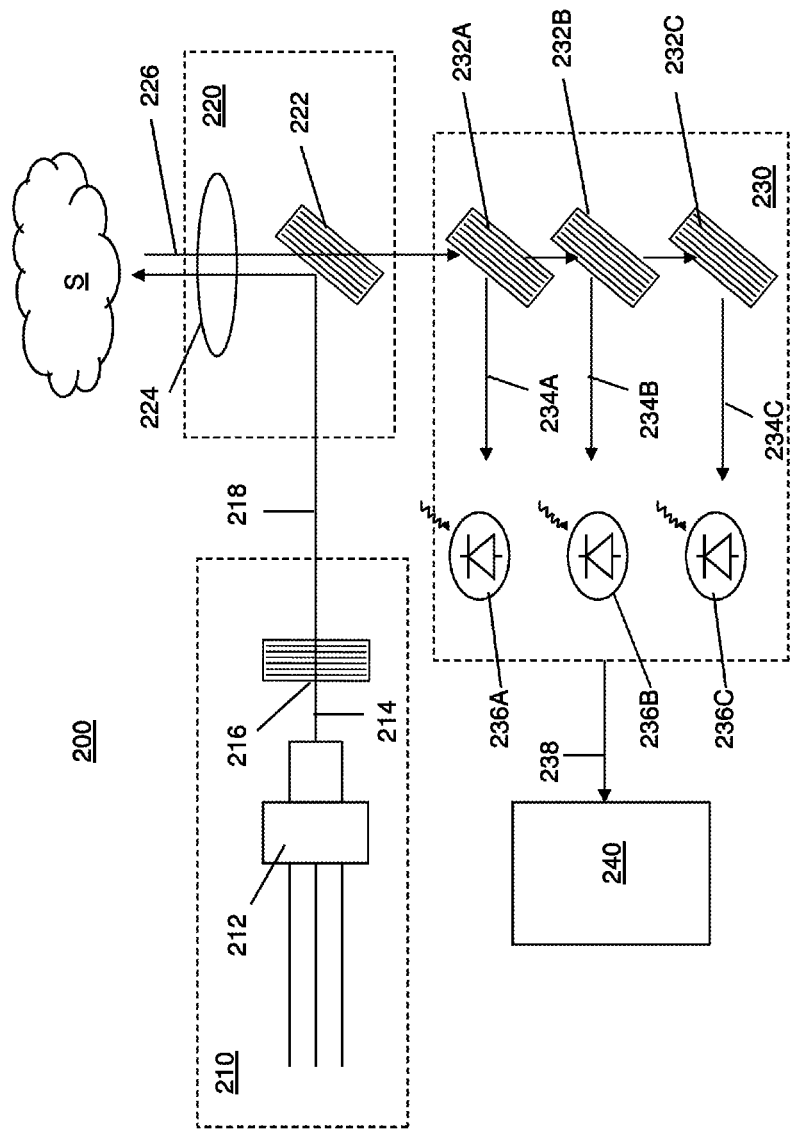
FIG. 3 is a diagrammatic view of a Raman tester that includes a plurality of three-dimensional Bragg grating elements.

FIG. 3 is a diagrammatic view of a Raman tester 200 that includes a plurality of three-dimensional Bragg grating elements. As shown, a laser source module 210 may include a laser source 212 and a Bragg grating element 216. The Bragg grating element may be adapted to condition the laser beam 214 emitted from the laser source 212, as described in detail above, to produce a Raman source beam 218.

The laser source module 210 may deliver the Raman source beam 218 to a beam delivery and signal collection module 220. The module 220 may include a Bragg grating element 222 having a Bragg grating recorded thereon that is adapted to direct the Raman source beam 218 to a Raman sampling head 224.

The Bragg grating element 222 may be further adapted to receive and deliver Raman scattered light 226 that is scattered from the sample S to a spectrum analysis module 230. As shown, the Bragg grating element 222 may be adapted to perform as a narrowband notch filter that allows passage of only certain bands of the Raman spectral range, e.g., where peaks for a given substance of interest may appear. As shown, a single Bragg grating element 222 may be used both to direct the Raman source beam 218 onto the sample S and to deliver Raman scattered light 226 that is scattered from the sample S to a spectrum analysis module 230. Alternatively, as illustrated in FIG. 4, a first Bragg grating element (such as one associated with a beam delivery and signal collection module 320) may be used to direct the Raman source beam onto the sample, and a second Bragg grating element 322 may be used to deliver the Raman scattered light to the spectrum analysis module.

The spectrum analysis module 230 may include one or more Bragg grating elements 232A-C that cooperate to demultiplex the Raman scattered light into a plurality of discrete Raman bands of interest 234A-C, and to deliver the Raman bands 234A-C into respective detectors 236A-C. The detectors 236A-C may be adapted to detect the presence of signal energy in the Raman bands 234A-C. The detectors 236A-C may produce a digital signal 238 that is representative of the energy in the several Raman bands. The spectrum analysis module 230 may pass the digital signal 238 to a digital signal processor 240. The signal 238 may be processed digitally to ascertain information about the Raman pattern. The DSP 240 may include signal processing software or a programmable logic circuit that is adapted to determine the qualitative and/or quantitative presence of the substances measured. That is, the DSP module may be adapted to determine whether a substance is present in the sample, and/or how much of the substance is presenting the sample.

One channel (say, 232A→234A→236A) of the spectrum analysis module 230 may be adapted to receive and monitor a background signal. Such monitoring enables the Raman spectra to be analyzed for quantitative information after the background noise level is subtracted from energy levels in the Raman bands (leaving a more accurate measure of the true scattered energy in each of the Raman bands). One or more Bragg grating elements that cooperate to allow passage or two or more passbands may be used. A first passband may be tuned to a desired Raman band, while the other passbands are tuned to bands where there is no Raman signal. Consequently, the ratio of signals from the respective passbands can provide a quantitative measurement of the Raman signal by subtraction of the background and fluorescence signals from the Raman signal.

Figure 4:
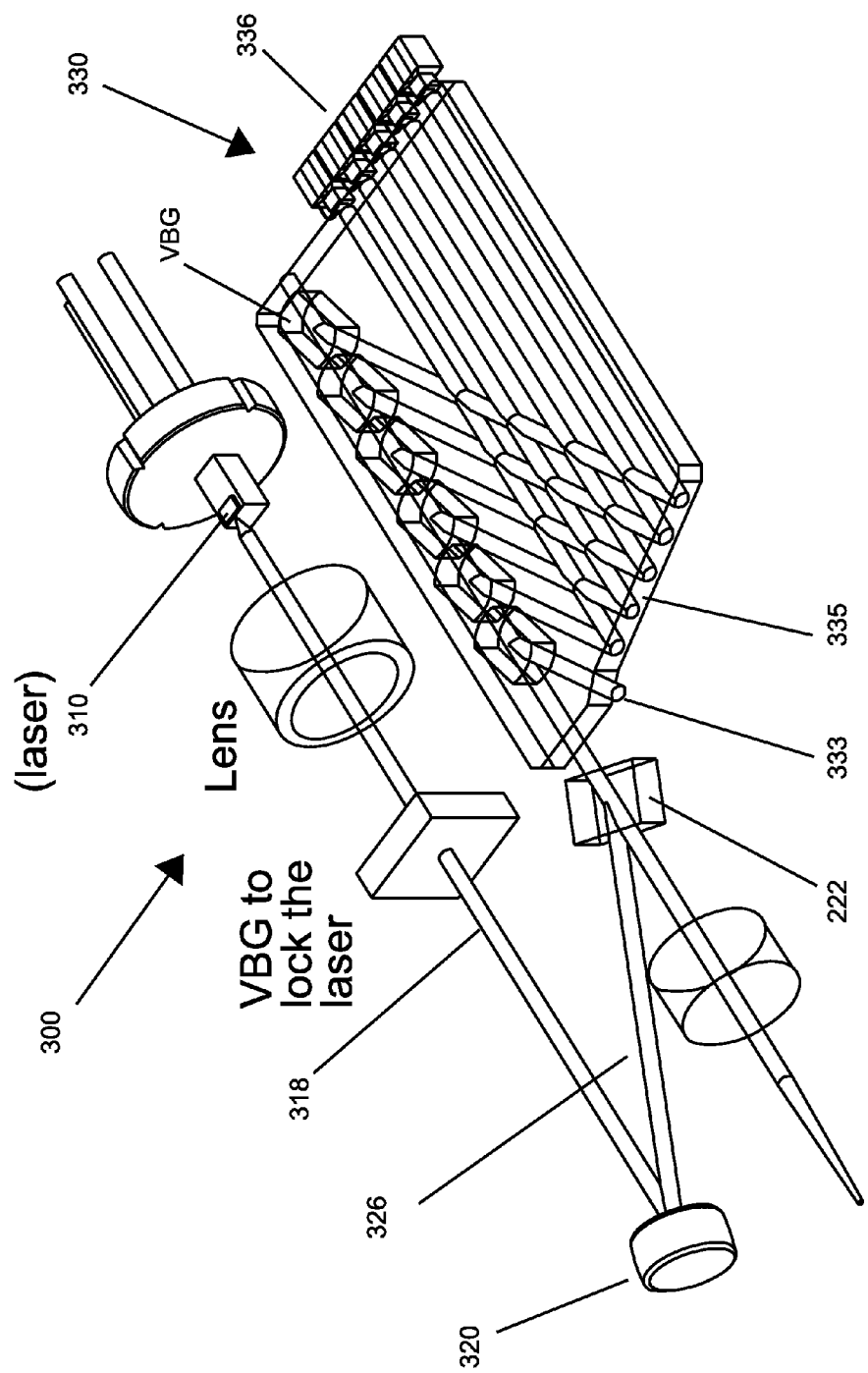
FIG. 4 depicts an example sensor packaged for commercial application.

FIG. 4 depicts an example sensor 300 packaged for commercial application. The example embodiment shown includes a laser source module 310, which may include a laser source and a Bragg grating element, as described above in connection with FIG. 3. The Bragg grating element may be adapted to condition the laser beam emitted from the laser source to produce a laser source beam 318. A lens may be provided to collimate the beam.

The laser source module 310 may deliver the laser source beam 318 to a beam delivery and signal collection module 320. As described above, the beam delivery and signal collection module 320 may include a Bragg grating element and a Raman sampling head. The Bragg grating element may have a Bragg grating recorded thereon that is adapted to direct the Raman source beam 318 to a Raman sampling head. The Bragg grating element may be further adapted to receive and deliver Raman scattered light 326 that is scattered from the sample (not shown in FIG. 4) to a spectrum analysis module 330. The light 326 may also pass via the second Bragg grating element 322 to the spectrum analysis module 330 and, for example, from the second Bragg grating element 322 through a lens 328.

The spectrum analysis module 330 may include a plurality of Bragg grating elements VBG that cooperate to separate respective Raman bands of interest. The VBGs may redirect the Raman bands to respective detectors 336. As shown, the Raman bands may be directed from the Bragg grating elements VBG via reflectors 335 to the detectors 336. The detectors 336 may be adapted to detect the presence of signal energy in the Raman bands. As shown, one channel 333 of the spectrum analysis module 330 may be adapted to receive and monitor a background signal as described in detail above.

As shown, such a sensor 300 may be a portable, compact device that is dedicated to detect a particular Raman spectrum of interest (e.g., a Raman spectrum for a substance expected to have peak energy in each of five bands). Note that such a sensor 300 may be about the size of a razor blade. Thus, such a monitor may be small and portable enough to be worn by a person or placed in open spaces, buildings, vehicles, tubes, pipes, or underground. Such a monitor may be designed to be operated remotely, and may be configured to be operated by a battery, from a grid or electrical network, or from some other power source such as solar cells.

It should be understood that a Raman monitor according to the invention may be adapted to monitor for more than one substance by having a sufficient number of spectral band monitors to detect the characteristic Raman spectra of more than one substance. Such "combination detectors" may be useful as "smoke" detectors in buildings or in security applications to screen for particular unwanted or harmful substances. Such combination detectors may also be useful to control manufacturing processes by monitoring hazardous by-products. Various modes of alarm, including audible sounds, visual cues, and vibrations, for example, may be employed to alert a user to the presence of a monitored substance.

Various embodiments of the invention have wide application in the field of monitoring for hazardous substances. Monitoring substances such as biohazards, explosives, poisons, and toxic gases using a Raman monitor is of interest to military and Homeland security applications. Law enforcement could use Raman monitors tuned to monitor illicit substances such as illegal drugs and contraband. Industrial quality could be monitored, with Raman devices monitoring the reactant and product streams of processes in the chemical, pharmaceutical, petrochemical, food, and materials industries. Industrial applications could also include monitoring discharge streams for hazardous effluents, whether gaseous, liquid or solid. Water purification plants could also benefit from Raman monitoring.

Raman spectral monitors can also be used to identify materials such as plastics, metals, minerals, and any other material that provides a characteristic Raman spectra. Possible medical applications using these Raman monitoring devices include diagnostics that involve the Raman spectra of various tissues or possible sampling to determine drug of toxin metabolism or detection of counterfeit drugs. In general, these Raman monitoring devices can be used to test almost any sample for the presence or absence of one of more substances with a Raman signature.

Figure 7:
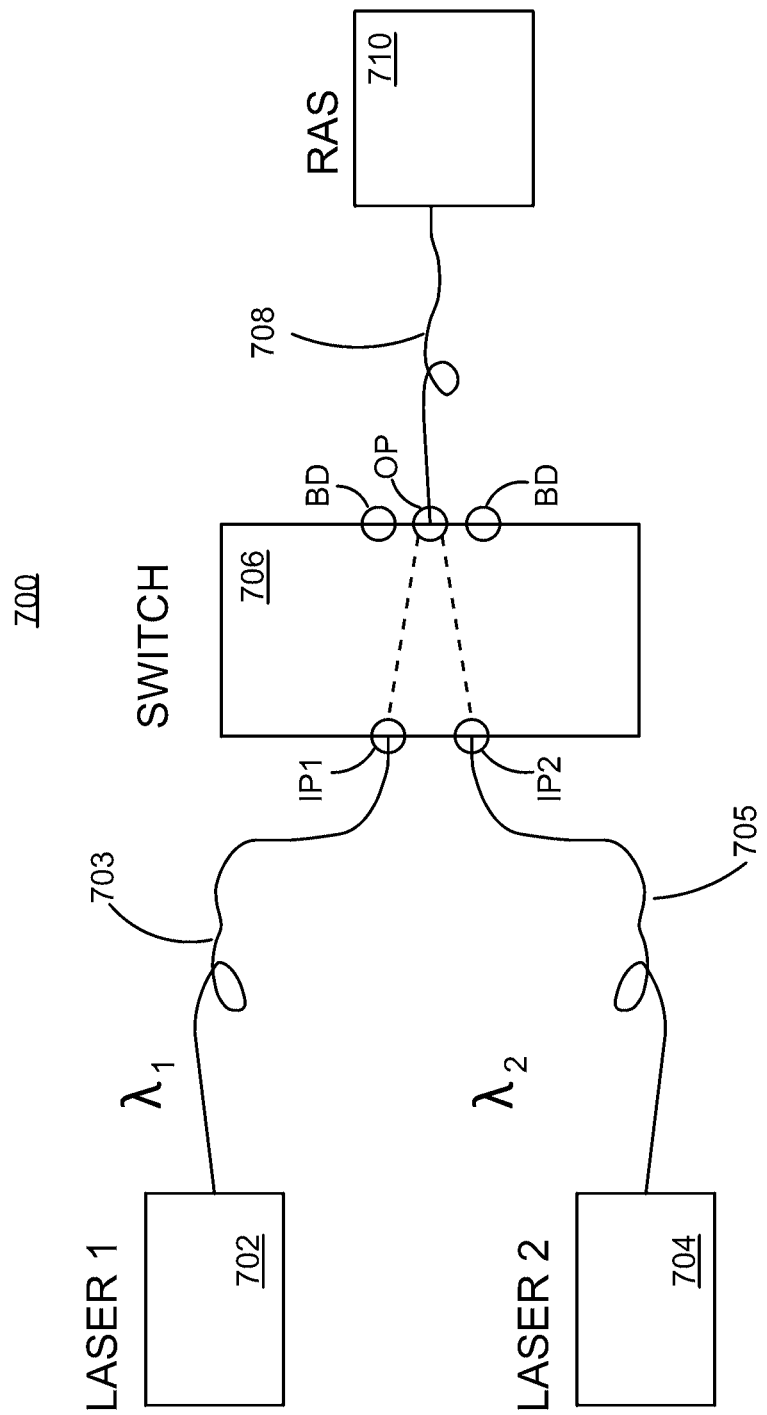
FIG. 7 is a block diagram of an example system for performing shifted excitation Raman spectroscopy (SERDS) that includes a plurality of laser sources and an optical switch.

FIG. 7 is a block diagram of an example 700 system for performing shifted excitation Raman spectroscopy (SERDS) that includes a plurality of laser sources 702, 704 and an optical switch 706. As shown, the system 700 may include a first laser source 702 having a first emission wavelength $\lambda_1$ and a second laser source 704 having a second emission wavelength $\lambda_2$. A separation between the first and second emission wavelengths $\lambda_2$-$\lambda_1$ may correspond to a width of a Raman band of a substance of interest.

The system 700 may also include an optical switch 706 that provides switching between the laser sources 702, 704, such that light emitted from the laser sources 702, 704 is delivered sequentially, e.g., alternatingly, to an output port of the optical switch 706. As shown, the optical switch may have one or more internal beam dumps BD, which may be in neutral positions.

The first laser source 702 may be optically coupled to a first input port $IP_1$ of the optical switch 706. For example, the first laser source 702 may be coupled to the first input port $IP_1$ of the optical switch 706 via a first optical fiber 703, as shown, or by any other beam delivery system. The second laser source 704 may be optically coupled to a second input port $IP_2$ of the optical switch 706. For example, the second laser source 704 may be coupled to the second input port $IP_2$ of the optical switch 706 via a second optical fiber 705, as shown, or by any other beam delivery system.

The system 706 may include a beam delivery system, such as an optical fiber, for example, that couples the output port OP of the optical switch 706 to a Raman analysis system RAS. The Raman anaylsis system RAS may be, for example, any of the systems described above. Thus, the output optical fiber 708 may couple the output port OP of the optical switch to a sample to be analyzed by means of Raman spectroscopy. For example, the sample may be analyzed to determine whether it is a substance of interest. Consequently, the sample may be illuminated sequentially, e.g., alternatingly, by light from each of the first and second laser sources 702, 704. Raman scattered light emanating from the sample may be collected and analyzed.

Figure 8:
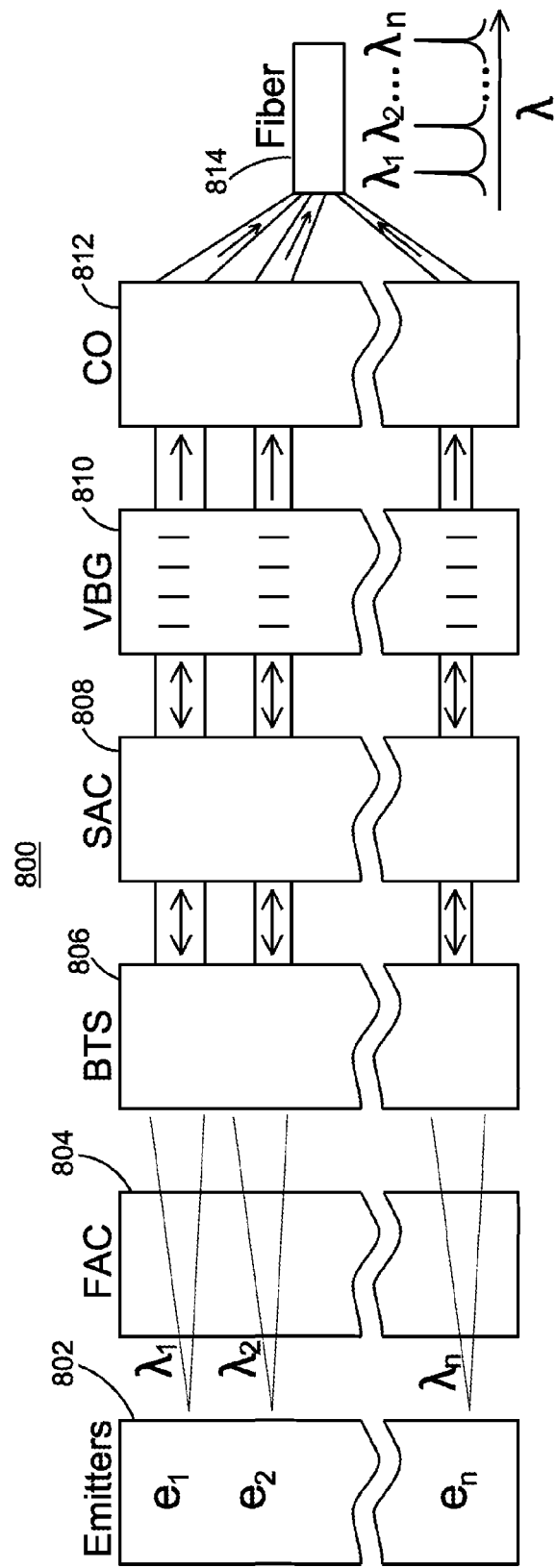
FIG. 8 a block diagram of an example system for performing SERDS that includes an ensemble of laser sources and a single output fiber.

FIG. 8 a block diagram of an example system 800 for performing SERDS that includes an ensemble 802 of laser sources $e_1, e_2, \ldots, e_n$ and a single output fiber 814. As shown, the system 800 may include an ensemble 802 of laser emitters $e_1, e_2, \ldots, e_n$, each of which may be individually addressable. Operation of the emitters $e_1, e_2, \ldots, e_n$ may be controlled by a laser driver (not shown), and driven in continuous or pulsed mode as desired. The emitters $e_1, e_2, \ldots, e_n$ may be operated simultaneously or sequentially relative to one another, as desired. Each of the emitters $e_1, e_2 \ldots e_n$ may be a respective p-n junction. The emitters $e_1, e_2 \ldots e_n$ may be respective p-n junctions in a single chip.

The ensemble 802 may include any number of laser emitters, preferably two or more. The emitters may operate at different wavelengths $\lambda_1, \lambda_2, \ldots, \lambda_n$. For example, as shown in FIG. N, the ensemble 802 may include a first laser emitter $e_1$ that emits laser light having a first wavelength, a second laser emitter $e_2$ that emits laser light having a second wavelength $\lambda_2$, and a third laser emitter $e_n$ that emits laser light at a third wavelength $\lambda_n$.

A separation between the first and second wavelengths $\lambda_2$-$\lambda_1$ may correspond to a width of a Raman band of a substance of interest. A separation between the second and third wavelengths $\lambda_n$-$\lambda_2$ may correspond to a width of a second Raman band of the substance of interest, or to a width of a Raman band of a second substance of interest. When the wavelengths are separated by the width of a Raman band, one wavelength is being used to sample the peak of the Raman line, while the other is being used to sample the valley. Thus, the signal-to-noise ratio of the difference spectrum may be maximized.

The system 800 may also include a Bragg grating element 810 that receives the laser light from the laser emitters $e_1, e_2, \ldots, e_n$. The Bragg grating element 810 may be a three-dimensional optical element having a Bragg grating recorded therein. The Bragg grating may be holographically recorded in a three-dimensional bulk of optical material, such as PTR glass, for example. The Bragg grating element 810 may include a plurality of Bragg gratings, each of which may have a respective period.

The Bragg grating element 810 may reflect a respective portion of the light it receives from each of the emitters $e_1, e_2, \ldots, e_n$ back into the emitters $e_1, e_2, \ldots, e_n$ as narrowband seeds that cause each of the emitters $e_1, e_2, \ldots, e_n$ to lase at its respective wavelength $\lambda_1, \lambda_2, \ldots, \lambda_n$. For this purpose, the Bragg grating may have a period that varies as a function of position along the longitudinal axis of the Bragg grating element 810.

The system 800 may also include an optical system 812 that directs light from the Bragg gratings into a beam delivery system 814, such as an optical fiber, for example. A combined beam delivered through the optical fiber 814 may contain light from each of the emitters $e_1, e_2, \ldots, e_n$. Thus, the output optical fiber 814 may couple the optical system 812 to a sample to be analyzed by means of Raman spectroscopy. For example, the sample may be analyzed to determine whether it is a substance of interest. The sample may be illuminated sequentially, e.g., alternatingly, by the light from the several laser sources. Raman scattered light emanating from the sample may be collected and analyzed.

The system 800 may also include a beam transformation system 806 ("BTS") that receives the laser light from the laser emitters $e_1, e_2, \ldots, e_n$. The Bragg grating element 810 may receive the laser light from the BTS 806. The BTS 806 may optically rotate images of the laser emitters $e_1, e_2, \ldots, e_n$ by 90 degrees. It may be desirable to rotate the image of the laser emitters $e_1, e_2, \ldots, e_n$ by 90 degrees to match the numerical aperture of the output optical fiber 814 on both axes; to make the beam parameter product of the combined beam that is input to the optical fiber 814 more symmetrical and therefore better matched to the fiber 814. Alternatively, the emitters themselves could be rotated or otherwise disposed relative to one another to achieve the desired beam parameter product without the need for a BTS 806.

A fast-axis collimator 804 may be disposed between the ensemble 802 of laser emitters $e_1, e_2, \ldots, e_n$ and the beam transformation system 806. A slow-axis collimator 808 may be disposed between the beam transformation system 806 and the Bragg grating element 810. The fast and slow axes of the laser emitters $e_1, e_2, \ldots, e_n$ may be chosen to optimize the beam parameter product of the combined output beam.

What is claimed:

1. Apparatus for performing Raman spectroscopy, the apparatus comprising:
   a first laser source having a first emission wavelength;
   a second laser source having a second emission wavelength, wherein a separation between the first and second emission wavelengths corresponds to a width of a Raman band of a substance of interest; and
   an optical switch that provides switching between the first and second laser sources.

2. The apparatus of claim 1, wherein the optical switch provides the switching between the first and second laser sources such that light emitted from the first and second laser sources is emitted alternatingly via an output port of the optical switch.

3. The apparatus of claim 2, wherein the optical switch has internal beam dump in a neutral position.

4. The apparatus of claim 3, comprising a first optical fiber that couples the first laser source to a first input port of the optical switch.

5. The apparatus of claim 4, comprising a second optical fiber that couples the second laser source to a second input port of the optical switch.

6. The apparatus of claim 3, comprising an output optical fiber that couples the optical switch to a Raman analysis system.

7. The apparatus of claim 6, wherein the output optical fiber is coupled to an output port of the optical switch.

8. The apparatus of claim 6, wherein the output optical fiber couples the optical switch to a sample to be analyzed to determine whether the sample is a sample of the substance of interest.

9. The apparatus of claim 8, wherein the sample is illuminated alternatingly by the light from the first and second laser sources, and Raman scattered light emanating from the sample is collected and analyzed to determine whether the sample is a sample of the substance of interest.

10. Apparatus for performing Raman spectroscopy, the apparatus comprising:
    an ensemble of individually addressable laser emitters, the ensemble comprising a first laser emitter that emits laser light having a first wavelength and a second laser emitter that emits laser light having a second wavelength, wherein a separation between the first and second wavelengths corresponds to a width of a Raman band of a substance of interest;
    a Bragg grating element that receives the laser light from the laser emitters, the Bragg grating element comprising a three-dimensional bulk of optical material having recorded therein a first Bragg grating having a first period and a second Bragg grating having a second period; and
    an optical system that directs light from the first and second Bragg gratings into an optical fiber,
    wherein a combined beam through the optical fiber contains light from each of the first emitter and the second emitter.

11. The apparatus of claim 10, further comprising a beam transformation system that receives the laser light from the laser emitters and rotates images of the laser emitters by 90 degrees, wherein the Bragg grating element receives the laser light from the beam transformation system.

12. The apparatus of claim 10, wherein each of the first and second laser emitters is a p-n junction.

13. The apparatus of claim 10, wherein the first and second laser emitters are respective p-n junctions in a single chip.

14. The apparatus of claim 10, wherein the first and second laser emitters are individually addressable to emit respective laser light sequentially.

15. The apparatus of claim 11, further comprising a fast-axis collimator between the ensemble of laser emitters and the beam transformation system, and a slow-axis collimator between the beam transformation system and the Bragg grating element.

16. The apparatus of claim 10, wherein the Bragg grating element reflects a respective portion of the light it receives from each of the emitters back into the emitters as a narrow-band seed that causes each of the emitters to lase at its respective wavelength.

17. The apparatus of claim 10, wherein the ensemble comprises a third laser emitter that emits laser light having a third wavelength, wherein a separation between the second and third wavelengths corresponds to a width of a second Raman band of the substance of interest.

18. The apparatus of claim 10, wherein the ensemble comprises a third laser emitter that emits laser light having a third wavelength, wherein a separation between the second and third wavelengths corresponds to a width of a Raman band of a second substance of interest.

19. The apparatus of claim 10, wherein the Bragg grating element has a longitudinal axis, and has recorded therein a Bragg grating having a period that varies as a function of position along the longitudinal axis of the Bragg grating element.

20. The apparatus of claim 10, wherein the output optical fiber couples the optical system to a sample to be analyzed to determine whether the sample is a sample of the substance of interest, wherein the sample is illuminated alternatingly by the light from the first and second laser sources, and Raman scattered light emanating from the sample is collected and analyzed to determine whether the sample is a sample of the substance of interest.

* * * * *